United States Patent [19]
Lehrman et al.

[11] Patent Number: 5,272,070
[45] Date of Patent: Dec. 21, 1993

[54] METHOD FOR THE PREPARATION OF CELL LINES PRODUCING MAN₃GLCN$_{ac}$2 ASPARAGINE-LINKED GYLCANS AND CELL LINES PRODUCED THEREBY

[75] Inventors: Mark A. Lehrman, Dallas, Tex.; Yucheng Zeng, Kansas City, Mo.

[73] Assignee: Board of Regents, The University of Texas System, Austin, Tex.

[21] Appl. No.: 667,317

[22] Filed: Mar. 8, 1991

[51] Int. Cl.⁵ .................. C12N 15/01; C12N 5/06
[52] U.S. Cl. .................. 435/172.1; 435/226; 435/240.2; 435/240.21
[58] Field of Search ............... 435/172.1, 240.2, 320.1; 536/27

[56] References Cited
U.S. PATENT DOCUMENTS

4,703,008 4/1987 Lin .................. 435/240.2

OTHER PUBLICATIONS

Zeng & Lehrman, J Biol Chem, 265(4):2296-2305, 1990.
Takeuchi et al., J Biol Chem, 265(21):12127-12130, 1990.
Kumar & Stanley, Mol Cell Biol, 9(12):5713-5717, 1989.
Spellman et al., J Biol Chem, 264(24):14100-14111, 1989.
Lehrman & Zeng, J Biol Chem, 264(3):1584-1593, 1989.
Stanley, Mol Cell Biol, 9(2):377-383, 1989.
Stanley & Chaney, Mol Cell Biol, 5(6):1204-1211, 1985.
Chaney & Stanley, J Biol Chem, 261:10551-10557, 1986.
Stanley, Ann Rev Genet, 18:525-552, 1984.
Gottlieb et al., J BIOL Chem, 250(9):3303-3309, 1975.
Darnell et al., Molecular Cell Biology, Scientific American Books, Inc., pp. 957-964, 1986.

Primary Examiner—Richard A. Schwartz
Assistant Examiner—James Ketter
Attorney, Agent, or Firm—Arnold, White & Durkee

[57] ABSTRACT

Disclosed is the preparation of eukaryotic cells which are capable of producing smaller and less heterogenic N-linked glycans, particularly glycans having the structure $Man_3GlcNAc_2$. In particular embodiments, CHO cells are produced having two particular defects in enzymes involved in N-linked glycosylation. The first defect, PIR, leads to an accumulation of $Man_5GlcNAc_2$-P-P-dolichol and thus lends resistance to glycosylation processing inhibitors such as castanospermine and swainsonine. The second defect involves a defect in the enzyme N-acetylglucosaminyltransferase I activity, and thus prevents the attachment of N-acetylglucosamine residues to oligosaccharide structures. About 70 to 75% of the N-linked glycans produced by cells of the present invention are thus in the form of $Man_3GlcNAc_2$, making these lines particularly well suited to the production of proteins, e.g., recombinant proteins such as EPO and t-PA, which one desires to have a smaller and more homogeneous N-linked glycan structure.

18 Claims, 5 Drawing Sheets

METHOD FOR THE PREPARATION OF CELL LINES PRODUCING MAN₃GLCN$_{ac}$2 ASPARAGINE-LINKED GYLCANS AND CELL LINES PRODUCED THEREBY

The government may own certain rights in the present invention pursuant to NIH grant RO1-GM-38545.

BACKGROUND OF THE INVENTION

1. Field of the Invention

The present invention relates generally to cell lines and particularly to methods and compositions for the development of cell lines which exhibit less heterogeneity in their asparagine-linked glycans, with most such glycans being produced in the form of Man$_3$GlcNAc$_2$.

2. Description of the Related Art

It is now well established that many important cell surface proteins and secretory proteins produced by eukaryotic cells contain one or several carbohydrate groups, and are thus said to be "glycosylated" (for a general overview see, e.g., Darnell et al., 1986). These carbohydrates serve many possible functions. For example, the addition of carbohydrate groups to a protein can affect the conformation of a polypeptide, making it more resistant to enzymatic degradation, or increase its solubility, due to the many hydroxyl groups present on carbohydrates. Further, some carbohydrate residues are important in directing the particular glycosylated protein to a particular location within the cell.

Importantly, carbohydrate residues have been found to play a potentially profound role in the pharmacology of various glycosylated proteins produced by cells, such as in the case of human tissue plasminogen activator (t-PA) and human erythropoietin (EPO) (Spellman et al., 1989; Takeuchi et al., 1990). Interestingly, it has been discovered that t-PA exists in two forms, depending on the presence (type I) or absence (type II) of carbohydrate at position Asn-184, with type II exhibiting a specific activity of about 30-50% greater than that of type I t-PA (Spellman et al., 1989). Similarly, in the case of EPO it was found that sequential removal of galactose and N-acetylglucosamine from the outer chain moieties of the desialylated Asn-type sugar chains raised the activity of the hormone up to four to five times that of intact EPO (Takeuchi et al., 1990).

The cellular mechanisms which underlie carbohydrate attachment to proteins is complex. In eukaryotes, sugars are commonly attached to one of four different amino acid residues and are classified as either O-linked (serine or threonine) or N-linked (asparagine). The structures of N- and O-linked oligosaccharides are very different, and different sugar moieties are found to be attached in each type. For example, in the case of N-linked oligosaccharides, the sugar residues are synthesized from a common precursor and subsequently processed. The precursor is a branched oligosaccharide containing three glucose, nine mannose and two N-acetylglucosamine molecules (GlcNAc) that is linked by a pyrophosphate residue to dolichol, a long-chain unsaturated lipid. The mannose residues are attached to the free amino group of asparagine by means of the two residues of GlcNAc.

The assembly process involves at least 16 enzymatic reactions to generate oligosaccharides attached to dolichol in pyrophosphate linkage and containing 2 residues of N-acetylglucosamine, 9 residues of mannose, and 3 residues of glucose (Kornfeld et al., 1985). This precursor is then transferred in its entirety to the amino group of asparagine through the action of oligosaccharide transferase inside the lumen of the rough endoplasmic reticulum. However, due to the action of various cellular enzymes, much heterogeneity is found to exist in the N-linked glycan, such as in terms of the number of mannose residues that are attached in "high mannose" structures, and in terms of the number, length, and terminal sugars of the branches of the "complex-type" structures.

Due to the importance of carbohydrate residues on the biological and physiological parameters of proteins, particularly the N-linked glycans, much research has been conducted in elucidating the mechanisms involved in glycosylation. In particular, various cell lines having one or more defects in their glycosylation mechanisms have been generated both as an aid I0 to understanding the underlying mechanism, and in attempts to provide cells which produce less heterogenic glycosylation patterns in proteins having N-linked glycans. The generation of proteins having less heterogeneity in the N-linked glycan structure is a particularly important goal, in that heterogeneity in the N-linked glycan is undesirable, such as in production and purification of useful glycoproteins (reviewed in Stanley, 1989), in biophysical studies of glycoproteins, or where one desires to modify the biological activity of the glycoprotein (see, e.g., Takeuchi et al., 1990).

Unfortunately, past attempts to develop cell lines which produce N-linked glycans that are smaller and less heterogeneous have met with only limited success. For example, in the C$_6$/36 mosquito cell line, which does not synthesize complex-type oligosaccharides, only about half of the N-linked glycans had the structure Man$_3$GlcNAc$_2$, with the remainder having heterogeneous compositions with 5 to 9 mannose residues (Hsieh et al., 1984). Presumably, the latter fraction resulted from incomplete trimming of precursors containing 9 mannose residues. A CHO line carrying the Lec1 and Lec6 mutations (Stanley, 1984; Hunt, 1980) was shown to produce glucosylated Man$_7$GlcNAc$_2$-P-P-dolichol which eventually gave rise to N-linked glycans with 4 mannose residues due to defective N-acetylglucosaminyltransferase I. However, there was also significant accumulation of oligosaccharides with 5-7 mannose residues, presumably due to incomplete trimming. Several other CHO lines have also been described carrying the Lec1 mutation in combination with others mutations (Stanley, 1989), but the smallest N-linked glycan produced by these cells had 5 mannose residues.

Accordingly, there is currently a need for methodology for the development of cell lines which are capable of producing N-linked glycans having a reduced heterogeneity. More specifically, there is a need for the development of cell lines that have the ability to produce N-linked glycans having greater proportions of glycans existing in the form of simplified structures such as Man$_3$GlcNAc$_2$. In particular, there is a need for cell lines which can be used as recombinant host cells for the production or recombinant glycoproteins having simplified glycosylation patterns, which may provide means of altering the underlying biologic parameters of the produced protein or improving the yield or purity of isolation.

SUMMARY OF THE INVENTION

The present invention, in a general and overall sense, attempts to address one or more of the foregoing or other shortcomings in the prior art by providing techniques for preparing cell lines which produce asparagine-linked glycans that have fewer saccharide residues than normal and have significantly reduced heterogeneity in their structure. The N-linked glycans which are produced by cell lines of the present invention are generally 5 sugar structures in the form of Man$_3$GlcNAc$_2$, as opposed to the more typical complex-type structures containing 11 or more sugars which are normally produced by cells. It is proposed that cell lines which are produced in accordance with the invention will provide various advantages over prior art cell lines, for example, in the preparation of recombinant proteins having improved biologic and pharmacologic properties, and reduced heterogeneity in the purified preparations.

In general, cell lines of the present invention will have certain defects in their N-linked glycosylation mechanisms which leads to the preferential production of Man$_3$GlcNAc$_2$ glycans rather than complex glycans comprised of N-acetylglucosamine (GlcNAc), galactose, mannose, fucose and sialic acid residues. In general, it has been found that cell lines produced in accordance with the invention will have at least 70% of their glycosylated asparagine residues linked to Man$_3$GlcNAc$_2$ oligosaccharides, and the remainder will have Man$_4$GlcNAc$_2$ or Man$_5$GlcNA$_2$ oligosaccharides.

In particular embodiments, cell lines of the present invention will have a first and second defect in their N-linked glycosylation mechanisms, wherein the first defect results in an accumulation of Man$_5$GlcNAc$_2$-P-P-dolichol, and the second defect will be one which results in defective N-acetylglucosaminyltransferase I activity. The first defect is exemplified by a defect referred as the "PIR" mutation, which refers to cells that are resistant to glycoprotein processing inhibitors. PIR cells are developed through resistance to glycoprotein processing inhibitors such as castanospermine, swainsonine and deoxymannojirimycin. By way of theory, it is believed that these cells have altered biosynthetic pathways for the preparation of dolichol-linked oligosaccharides, which reduces or eliminates their requirement for various processing enzymes during the production of normal mature asparagine-linked oligosaccharides.

As noted, the second defect results in a defective N-acetylglucosaminyltransferase I activity. It is believed that any defect that will result in a relative decrease in the N-acetylglucosaminyltransferase I activity will provide advantages in accordance with the present invention. Cells with such a defect generally do not transfer, or have a reduced ability to transfer, N-acetylglucosamine residues from UDP-GlcNAc to glycopeptide or glycoprotein acceptors. The existence of the second defect will generally be accompanied by resistance to agglutinins such as Phaseolus vulgaris erythroagglutinin and leucoagglutinin (PHA-E and PHA-L, respectively) and Lens culinaris agglutinin (LCA). By way of theory, it is believed that this resistance is due to the absence of target oligosaccharides, the means by which these agglutinins bind to cells and exert their toxicity.

Again by way of theory, it is proposed that these two defects act in concert to produce N-linked glycans having reduced heterogeneity. The first defect results in an accumulation of Man$_5$GlcNAc$_2$-P-P-dolichol, and therefore results in a 7 sugar structure being N-linked, rather than the more typical 14 sugar structure. Normal processing mannosidases convert the 7-sugar structure to a 5-sugar structure (Man$_3$GlcNAc$_2$). Without the defect in N-acetylglucosaminyltransferase I activity, this enzyme would act to add additional GlcNAc residues to the 5 sugar structure, and thereby further allow the incorporation of additional sugars such as galactose and fucose and sialic acid moieties. However, when the N-acetylglucosaminyltransferase I activity is compromised, the addition of these residues does not take place, resulting in accumulation of Man$_3$GlcNAc$_2$.

The inventors have found that in the double mutants prepared in accordance with the invention, the 2 mannose residues are efficiently removed by mannosidase action from 70% to 80% of the oligosaccharides. Thus, it is believed that approximately 70% to 80% of the N-linked glycans will typically be in the form of Man$_3$GlcNAc$_2$, whereas the remaining 20–30% will be in the form of Man$_5$GlcNAc$_2$ or Man$_4$GlcNAc$_2$ In no case would the product of N-acetylglucosaminyltransferase I action be expected.

The most preferred cell lines for use in accordance with the present invention will be so called CHO-K1 cells, which refers to Chinese hamster ovary cells. These cells are preferred in that they have been found quite amenable to the selection of cell lines which exhibit the desired defects, and are in fact employed quite extensively in industry, such as in the production of recombinant proteins. Furthermore, CHO cells are preferred because faithful synthesis of dolichol-linked oligosaccharides with 14 sugars by these cells is believed to be important for the first step of the process, i.e., the creation of a PIR mutation.

However, it is believed that other cell lines can be employed for the selection of double mutants in accordance with the invention, so long as the vast majority of the dolichol-linked oligosaccharides are in the 14-sugar form instead of smaller intermediates with, for example, 7–9 sugars. The presence of moderate amounts of such intermediates could hinder creation of the PIR mutation, in which all the intermediates have 7 sugars.. In this regard, it is proposed that most cell types can be employed in the practice of the invention, because most animal cells synthesize predominantly 14-sugar dolichol-linked oligosaccharides. It should be pointed out, though, that initial attempts to introduce the appropriate defects into COS-1 cells have not been successful, presumably because the COS-1 cells normally have some dolichol-linked oligosaccharides with fewer than 14 sugars.

In other embodiments, cell lines of the present invention may be defined as cells which have properties which include 1) resistance to the action of glycoprotein processing inhibitors such as castanospermine or swainsonine; 2) resistance to the action of agglutinins, such as PHA-E, LCA or PHA-L, independent of the presence of swainsonine; and 3) which produce Man$_3$GlcNAc$_2$ asparagine-linked glycans. As used herein, the term "resistance" is intended to refer to relative resistance in that the cells will be more resistant to glycoprotein processing inhibitors or agglutinins than the parental cells. Generally speaking, cells of the present invention will be resistant to at least 100 µg/ml swainsonine and 1000 µg/ml castanospermine. With respect to resistance to agglutinins, cells of the present invention will typically be resistant to at least 200 µg/ml of LCA, PHA-E or PHA-L and more typically.

It is proposed that the cell lines of the present invention will be particularly useful as recombinant host cells, particularly recombinant host cells that produce glycosylated recombinant proteins, such as erythropoietin (EPO), tissue plasminogen activator (t-PA), various "glycoprotein" hormones, and the like. In general, it is proposed that host cells of the present invention will be applicable to the production of any recombinant protein wherein less heterogeneity and minimal complexity in the N-linked glycan structure is desirable.

Methods for providing cell lines in accordance with the invention are relatively straight forward and reproducible. In general, these methods include first, culturing a population of cells which produce N-linked glycans, and selecting from these cells, cells that are resistant to one or more glycoprotein processing inhibitors (e.g., PIR cells). Then, from these PIR cells, cells are selected that are resistant to an agglutinin such as PHA-E, wherein the resistance is independent of the presence of swainsonine, and resistant cells are then cultured to provide cell lines producing $Man_3GlcNAc_2$ asparagine-linked glycans.

The first step simply involves the selection of the cell type into which one desires to introduce the various defects. As noted, this can be virtually any cell which has a glycosylation capability and thus which produces N-linked glycan. Preferred will be the CHO-K1 cell line. However, most animal cell lines that synthesize predominantly 14-sugar dolichol-linked oligosaccharides should be suitable.

The second step involves selecting cells which are resistant to one or more glycoprotein processing inhibitors, such as castanospermine or swainsonine, to provide a cell culture of PIR cells. In particular embodiments, one may select PIR cells by first selecting conditions under which the glycoprotein processing inhibitors are slightly toxic in a concentration dependant manner so as to reduce growth rate but not eliminate the culture. After the culture recovers, then the cells are grown in increasing amounts of one of the foregoing glycoprotein processing inhibitors until resistant cells are realized.

Typically, resistant cells will be those which can tolerate at least 1000 μg/ml castanospermine or 100 μg/ml swainsonine. Often it may be necessary to develop specific conditions under which the growth of normal cells is inhibited by these compounds. The inventors have found that the lectin concanavalin A (ConA) is particularly useful for this purpose, in that the processing inhibitors will stimulate the cells to express additional Con A binding sites on their surfaces and therefore become more sensitive than untreated cells to the toxic effects of Con A. The concentration of Con A required for this effect will vary from cell type to cell type and study to study but will generally be within the range of 5 to 15 μg/ml.

Thus, through the combined use of lectins such as ConA and glycoprotein processing inhibitors that would inhibit the growth, but not kill the cells, it is possible to gradually select cells in which the action of the glycoprotein processing enzymes has been altered. These cells may then be cultured in the selective medium to ensure that the defect is stable.

Next, in order to introduce the second defect resulting in defective N-acetylglucosaminyltransferase I activity, cells bearing the PIR mutation are selected to obtain clones that spontaneously acquire PHA-E resistance, independent of swainsonine. The development of such cells can be aided by subjecting the PIR cells to selection in the presence of agglutinins such as PHA-E, PHA-L, LCA or any other toxic lectin that recognizes "complex-type" or "hybrid-type" oligosaccharides. In preferred embodiments, PIR cells are cultured in the presence of PHA-E in amounts ranging from 15 to 50 μg/ml, preferably about 20 μg/ml, together with about 1 μg/ml of swainsonine. The swainsonine is included because other types of mutations which could be desired can also be obtained in the same step. However, because the desired cells have sainsonine-independant lectin resistance, addition of the swainsonine at this stage is not necessary.

Cells which survive this incubation are preferably reselected under the selective conditions for several passages. The end results will be the development of a cell line that is resistant to high levels of LCA, PHA-E or PHA-L, such as 200 μg/ml, and which has defective N-acetylglucosaminyltransferase I activity. To ensure that this is the case, though, it is suggested that one screen the cells so produced to ensure that the PHA-E, PHA-L or LCA resistance is independent of the presence of swainsonine. Also, it is also suggested that one demonstrate that the resistant lines are both defective for N-acetylglucosaminyltransferase I by independant means and that the lines continue to make 7-sugar dolichol-linked oligosaccharides.

BRIEF DESCRIPTION OF THE DRAWINGS

FIG. 1 (parts A and B). Effect of swainsonine (SW) and oastanosoermine (Cs) on the bindino of ConA-horseradish peroxidase to CHO. CsR-1000, and SwR-100 cells. CHO cells (closed circles), CsR-1000 cells (closed squares), and SwR-100 cells (closed triangles) were incubated in the presence of increasing concentrations of swainsonine (top panel) or castanospermine (bottom panel) as described in Example I. The numbers adjacent to each curve indicate the ratio of binding at the highest concentration of inhibitor to binding in the absence of inhibitor. Binding of the ConA-horseradish peroxidase conjugates was normalized to cell mass as judged by the binding of crystal violet. In general, no variation of crystal violet binding was noted for any cell type under any condition.

FIG. 2. Processing pathways in PIR-P3 and PIR-P8 cells. Mannosyl and N-acetylglucosaminyl residues are noted by the abbreviations M and Gn, respectively, and the glycosidic linkages of the dolichol-P-P-oligosaccharide are indicated. The effect of the PIR (processing inhibitor resistance) mutation is to block assembly of dolichol-P-P-oligosaccharides at the pentamannosyl stage. After transfer to protein by oligosaccharyl transferase (OT), two mannose residues are removed by deoxymannojirimycin (Dmn)-sensitive mannosidases. The trimannosyl oligosaccharide (boxed) accumulates in PIR-P3 and PIR-P8 cells due to the absence of GlcNAc transferase I. Only the trimannosyl oligosaccharide ($Man\alpha1,3(Man\alpha1,6)Man\beta1, 4GlcNAc\beta1,4Gl$-cNAc) can be cleaved by endoglycosidase D (endo D) as shown.

FIG. 3 (parts A-E). HPLO analysis of N-glycananse-sensitive oligosaccharides. Oligosaccharides were cleaved from [$^3$H]mannose-labeled glycoproteins with N-glycanase and fractionated by HPLC as described in the methodology section of Example II. The sources and amounts of [$^3$H]-labeled material loaded were:(A) control CHO cells (1900 c.p.m.), (B) PIR cells (5300 c.p.m.), (C) PIR-P3 cells (9000 c.p.m.) (D) PIR-P8 cells (8800 c.p.m.), and (E) PIR-P8 cells treated with 100 ug/ml deoxymannojirimycin during labeling (12500 c.p.m.). All oligosaccharides generated by N-glycanase cleavage contain 2 residues of N-acetylglucosamine;

peaks are labeled to reflect the number of mannose residues per oligosaccharide chain as determined by comparison with standards obtained by weak acid cleavage of known samples of dolichol-linked oligosaccharides.

FIG. 4(parts A-E). PHA-L chromatography of glycopeptides. [$^3$H]mannose-labeled glycopeptides were prepared by pronase digestion as described in the methodology section of Example II. Glycopeptides were dissolved in a volume of 0.1 ml and applied to a 0.3 cm × 30 cm column of PHA-L agarose, approximately 4 mg/ml. Fractions of 0.5 ml were collected and counted. Glycopeptides were obtained from (A) control CHO cells, 13000 c.p.m., (B) PIR cells 15000 c.p.m., (C) 15B cells, 33000 c.p.m., (D) PIR-P3 cells, 18060 c.p.m., (E) and PIR-P8 cells, 18700 c.p.m.

FIG. 5(parts A-D). Endoglycosidase D digestion of glycopeptides. [$^3$H]mannose-labeled glycopeptides were prepared by pronase digestion and treated with endoglycosidase D as described in the methodology section of Example II. Digests were diluted to a volume of 0.13 ml and applied to a 1 cm × 47 cm column of Biogel P-4 equilibrated in 0.1 M ammonium bicarbonate. Fractions of 1.0 ml were collected and 25 ul portions were counted. The remaining portions of released oligosaccharides were applied to HPLC columns. Undigested peptides were found to elute near fraction 10 whereas released oligosaccharides eluted near fraction 25. Approximately 50000 c.p.m. of glycopeptides from the following cells were loaded: (A) control CHO cells (B) PIR cells (C) PIR-P3 cells and (D) PIR-P8 cells.

DETAILED DESCRIPTION OF THE PREFERRED EMBODIMENTS

The present invention is based on the inventors finding that cells lines can be engineered to produce a less heterogenic pattern of N-linked glycosylation, through the introduction of various defects in their cellular glycosylation mechanisms. In the normal case, N-linked glycosylation proceeds first through the production of a fourteen sugar structure, the dolichol pyrophosphate oligosaccharide precursor, which includes two N-acetylglucosamine residues (GlcNAc), nine mannose residues, and three glucose residues. Then, this precursor is transferred en bloc by oligosaccharide transferase to the nascent polypeptide chain at specific tripeptide sequences (Asn-X-Ser or Asn-X-Thr) at the lumenal surface of the rough endoplasmic reticulum (ER).

In the normal case, during transfer of the protein from the rough ER to the trans golgi, the attached oligosaccharide normally undergoes extensive processing by at least fifteen discrete glycosylation processing enzymes. For example, all of the glucose residues, and all but five of the mannose residues, are typically removed from the attached oligosaccharide structure during processing, followed by the subsequent addition of an outer row of one GlcNAc residue through the action of N-acetylglucosaminyltransferase I. Then, two more mannoses are removed, and GlcNAc, galactose and sialic acid residues are added, to complete what can be an eleven or more sugar structure attached to certain asparagine moieties on the secreted protein product.

However, different proteins and different cell types will exhibit a high degree of heterogeneity from one N-linked glycan to another. Heterogeneity among N-lined glycans results from two factors. First, after transfer to protein there may be incomplete trimming of nine-mannose precursor oligosaccharides (Hubbard, 1988). Six mannose residues are normally removed during formation of complex-type oligosaccharides; otherwise, hybrid and high mannose structures are made. Second, structural heterogeneity can result during branch formation by glycosyltransferases in the Golgi complex (Kornfeld, 1985). In this case there can be variability in the number, length, and terminal sugars of the branches of complex oligosaccharides. To minimize the size and structural heterogeneity of N-linked glycans it is therefore necessary both to optimize the removal of mannose residues and limit branch formation by glycosyltransferases.

The present invention involves the introduction of two separate defects in the foregoing cellular glycosylation mechanisms, which serves to limit the size of the N-linked glycan and, indeed, reduce the subsequent heterogeneity. The first defect, exemplified by the so-called PIR mutation, leads to an accumulation of the seven sugar structure, Man$_5$GlcNAc$_2$-P-P-dolichol. Thus, in PIR cells production of a seven sugar precursor is favored over that of the more typical fourteen sugar dolichol pyrophosphate precursor, and this seven sugar precursor is the structure that is likely transferred to the polypeptide. It is found that once the seven sugar structure is attached to the polypeptide, two of the five remaining mannose residues are removed in the Golgi through the action of mannosidases, leaving the five sugar structure, Man$_3$GlcNAc$_2$, attached to the protein.

However, in cells of the present invention, there is a second defect, which involves N-acetylglucosaminyltransferase I, the enzyme responsible for the subsequent addition of a single GlcNAc residue to the oligosaccharide complex. Due to the defect in N-acetylglucosaminyltransferase I, subsequent addition of all other sugar residues to the oligosaccharide is suppressed. Thus, because there is no subsequent attachment of sugar residues to the glycan, this ultimately results in an N-linked glycan having only five sugars, rather than the more typical 11 or more sugar structure. Surprisingly, the inventors have found that up to 60 to 80% (typically 70–75%) of the N-linked glycans exist in the Man$_3$GlcNAc$_2$ form. This is surprising because one could not predict in advance that the two mannose sugars would be removed efficiently by mannosidases to give the five sugar structure. Thus, is was possible that most of the oligosaccharides could have remained in the 7-sugar form.

Techniques for successful introduction of the first defect, which leads to an accumulation of the seven sugar structure, Man$_5$GlcNAc$_2$-P-P-dolichol, has been previously described by Lehrman et al., 1989. This defect, which is exemplified by the so called PIR mutation, involves the selection of cells which are resistant to various specific inhibitors of glycosidases, such as swainsonine and castanospermine. Swainsonine is the active component of locoweed, and acts both by inhibiting lysosomal α-mannosidase as well as the Golgi enzyme mannosidase II. Castanospermine acts by inhibiting glucosidases I and II.

As described in the foregoing article as well as in Example I of the present specification, the inventors have developed conditions using concanavalin A (ConA) wherein these inhibitors are toxic in a concentration dependant manner to cells. These conditions are then employed to gradually select cells that are resistant to increasing concentrations of these inhibitors. It was found that the resistant cells did not respond to the selections by altering properties or expression of the glycosidases in question, but rather by altering their biosynthetic pathway for dolichol-linked oligosaccharides. This had the effect of reducing or eliminating the requirement for the processing enzymes during the production of normal mature asparagine-linked oligosaccharides.

While the inventors typically employ glycosylation processing inhibitors such as swainsonine or castanospermine to select for PIR cells, it is believed that the invention is not limited to these substances. For example, the inventors propose that substances such as deoxynojirimycin, mannostatin or any of a number of inhibitors of glucosidase I, glucosidase II or mannosidase II, can be successfully employed for this purpose, so long as one tests the selected cells to ensure that there is an accumulation of $Man_5GlcNAc_2$-P-P-dolichol.

As noted above, the second defect of the present invention involves a defect in N-acetylglucosaminyltransferase I. The selection of PIR cells having a defect in this enzyme is achieved generally through the use of an agglutinin such as Phaseolus vulgaris erythroagglutinin and leucoagglutinin (PHA-E and PHA-L), or Lens culinaris agglutinin (LCA), to select resistant cells. The selection and use of PHA-E in the following examples was somewhat arbitrary, and it is believed that, in principal, any toxic lectin which is specific for "complex-type" or "hybrid-type" structures will work. It is proposed that this selection step relies on the fact that those cells having attached to their surfaces N-linked oligosaccharide structures of five sugars (i.e., $Man_3GlcNAc_2$) will be more resistant to the action of, e.g., PHA-E, than will those cells having a more complex sugar structures. Thus, through this procedure, cells which produce the less complex sugar structure will be selected. It is found that these cells in fact have a defect in N-acetylglucosaminyltransferase I, as evidenced by the fact the cells are PHA-E resistant, independent of the presence of swainsonine, and that they fail to complement a cell line (e.g., 15B) with a known defect in N-acetylglucosaminyltransferase I.

In general, this approach requires a cell line which has complex-type oligosaccharides on it surface, and accumulates mainly 14-sugar dolichol-linked oligosaccharides in the endoplasmic reticulum. The first selection is designed to isolate useful mutants (PIR) with a complete loss of the 14-sugar form with the resulting accumulation of a majority (100% is not possible due to other interfering cellular reactions) of 7-sugar forms. Cells such as COS-1 cells which normally accumulate both 7 and 14-sugar forms are able to survive the first selection, complicating the isolation of useful mutants. In this case, it may still be possible to isolate PIR mutants if the selection conditions are carefully adjusted.

The first selection combines Con A with a glycosidase inhibitor (such as castanospermine or swainsonine, or any glucosidase I, glucosidase II, or mannosidase II inhibitor) that blocks oligosaccharide processing so as to increase the number of Con A-binding structures on the cell surface. Each component alone is used at nontoxic concentrations but together they act synergistically to become toxic to normal cells but not the desired mutants (PIR).

The second selection starts with PIR cells, which express essentially normal "complex-type" structures on their surfaces. These cells are selected for spontaneously-occurring mutations (PIR-P) that result in diminished binding of lectins that bind complex-type structures. This was accomplished by isolating cells that were resistant to PHA-E resistance. For experimental reasons involving the inventors' research, the second selection was actually done with transfection of genomic DNA and inclusion of swainsonine, but these two modifications are not necessary (and are actually undesirable) if the goal is to isolate PIR-P cells. The two modifications were included for isolation of the PIR gene, which is not relevant to this application.

PIR-P cells can arise by several types of glycosyltransferase mutations. The ones that will be useful (five-sugar asparagine-linked glycans) must be specifically defective for N-acetylglucosaminyltransferase I. This must be confirmed in candidate PIR-P colonies by an independent method. The inventors did this by a genetic complementation test. Of the original eight PIR-P clones, only two were shown to be of the correct type. The remaining six were not characterized sufficiently.

In principle, the first and second selections involve lectin binding to cells. Thus, the desired mutant clones can be identified by lectin-dependent methods, for example: lectin toxicity during cell culture, fluorescence-activated cell-sorting with fluorescent lectins, fluorescence-assisted cell analysis and manipulation in culture dishes, and lectin-affinity chromatography.

The following examples set forth preferred modes of the inventors for carrying out the practice of the invention. In light of the present disclosure, it will be appreciated by those of skill in the art that various modifications and changes can be made in the following methodology without departing from the spirit and scope of the invention. For example, while the following disclosure is set forth in terms of CHO cells, it is believed that the techniques will be applicable to other cell lines. Moreover, while the prophetic use in connection with the expression of recombinant EPO or t-PA is disclosed, it will be apparent that these cell lines will be useful in connection with any protein which one desires to be produced in a less heterogenic glycosylated form. These and all other modifications that are apparent from this disclosure in light of the level of skill in the art are intended to be within the scope of the invention.

EXAMPLE I

Preparation of CHO Cells Resistant to Glycoprotein Processing Inhibitors

As a first step toward the preparation of cells in accordance with the invention, the inventors have developed CHO cells that are resistant to glycoprotein processing inhibitors, so-called PIR cells (see generally, Lehrman et al., 1989). PIR cell lines were developed by culturing normal CHO cells in the presence of increasing amounts of castnospermine ("CsR" cells) or swainsonine ("SwR" cells). These cells had normal levels of glucosidase II and mannosidase II and appeared to have no major structural alterations in their surface asparagine-linked oligosaccharides.

Interestingly, the CsR and SwR cells were each pleiotropically resistant to castanospermine and swainsonine, and slightly resistant to deoxymannojirimycin, an inhibitor of mannosidase I. This resistance was not due to the multiple-drug resistance phenomenon. Both the CsR and SwR cell populations synthesized $Man_5GlcNAc_2$ in place of $Glc_3Man_9GlcNAc_2$ as the major dolichol-linked oligosaccharide. This defect was not due to a loss of mannosylphosphoryldolichol synthetase. Furthermore, the $Man_5GlcNAc_2$ oligosaccharide was transferred to protein and appeared to give rise to normal mature oligosaccharides. Thus, the CsR and SwR cells achieved resistance to castanospermine, swainsonine, and deoxymannojirimycin by synthesizing altered dolichol-linked oligosaccharides that reduced or eliminated the requirements for glucosidases I and II and mannosidases I and II during the production of normal asparagine-linked oligosaccharides.

A. MATERIALS AND METHODS

1. Reagents

F-12 powdered medium, calf and fetal bovine serum, trypsin-EDTA, and a penicillin/streptomycin mixture were from Gibco. Crystal violet solution (1%) was from Difco. Castanospermine, deoxymannojirimycin, and endoglycosidase H were from Genzyme. Endoglycosidase F, peptide:N-glycosidase F. and yeast α-glucosidase were from Boehringer Mannheim. Acetonitrile (HPLC grade) was from Burdick and Jackson. Micropak AX-5 columns (30 cm) were from Varian Associates. Bio-Gel P-4 resin was from Bio-Rad. Concanavalin A, (Con A), Lens culinaris agglutinin (PHA-L) Phaseolus vulgaris erythroagglutinin (PHA-E), swainsonine, Pronase E, adriamycin, colchicine, vincristine, vinblastine, Amberlite MB-3, sodium borohydride, Nonidet P-40, o-phenylenediamine, glutaraldehyde, and paranitrophenyl glycosides were from Sigma. [2-$^3$H]Mannose (23.5 Ci/mmol), guanosine diphosphate [3,4-$^3$H]mannose (29.1 Ci/mmol), and [$^3$H]sodium borohydride (0.32 Ci/mmol) were from Du Pont-New England Nuclear.

Some oligosaccharide standards were prepared by incubating mutant CHO cells deficient in various enzymes with [$^3$H]mannose and isolating protein-bound oligosaccharides by endo H digestion (Tabas et al., 1982). Man$_5$GlcNAc and Man$_8$GlcNAc were isolated from clone 15B and clone 6 cells, respectively. In addition, Glc$_3$Man$_9$GlcNAc were prepared similarly from castanospermine-treated normal CHO cells. Chitobiose (Sigma) and maltooligosaccharide standards (Pfanstiehl) were radiolabeled with $^3$H as described by Mellis et al., 1981.

2. Cell Culture Techniques

CHO-K1 cells were routinely grown in F-12 medium containing 15 mM HEPES adjusted to pH 7.2 with sodium hydroxide, supplemented with 100 units/ml penicillin, 100 μg/ml streptomycin, 2% fetal bovine serum, and 8% calf serum, in a water-saturated 5% carbon dioxide atmosphere at 37° C. During selections with castanospermine, deoxymannojirimycin, or swainsonine, cells were grown in the same medium but with 10% fetal bovine serum and no calf serum. Selections were done in small culture vessels (Costar), beginning with 60-mm dishes and ending with 6-mm wells of 96-well plates in the final stages of selection. During selections, cells were plated at densities such that confluent monolayers would result after 7 days of growth if no ConA or drug was added. Once resistant cells were obtained, they were maintained in growth medium without ConA or inhibitors. However, they were reselected every 4 to 6 months to maximize resistance in the population.

For preparation of membranes, 4×10$^5$ normal or resistant cells were plated in 100-mm dishes and harvested after 4 days of growth. To assess the effects of different conditions on colony formation, cells were plated into wells of 24-well or 48-well plates containing medium with various concentrations of glycosylation inhibitor, lectin, or drug. Empty wells in the plate were filled with phosphate-buffered saline to minimize evaporation from the wells containing cells. After growth for 5-8 days, the medium was discarded, the wells were rinsed with phosphate-buffered saline, and the colonies were stained with 1% crystal violet solution.

Inhibitors used in selections were sterilized by mixing with 70% ethanol, dissolved with the addition of water, divided into aliquots, evaporated to dryness, and stored at −20° C. They were dissolved in culture medium containing ConA as needed. ConA used for selections was stored in aliquots at −20° C. as a 5 mg/ml solution in PBS. After thawing, the ConA was added directly to culture medium which was then sterilized by filtration. The remainder of the aliquot of ConA was discarded. Before use, medium containing ConA was allowed to equilibrate for 2 h at 37° C. or for 20 h at 4° C. to allow interactions between the lectin and serum glycoproteins to stabilize. The medium was stored at 4° C. and used within 2 weeks of adding the lectin. Each of the inhibitors appeared to be stable for the duration of the experiments in which they were used.

3. Preparation of Membranes

Membranes were prepared from cellular homogenates as described Lehrman et al., 1988. These membranes contained material that remained suspended at 1,500 X g for 5 min and then sedimented at 100,000 X g for 1 h.

4. Enzyme Assays

Mannosylmonophosphoryldolichol synthetase (Man-P-Dol synthetase) was assayed by incubating 20 μg of membrane protein in the presence of 5 mM MnCl$_2$, 10 mM MgCl$_2$, 64 mM Tris-Cl, pH 7.4, 105 mM NaCl, and 0.1 μCi of GDP-[$^3$H]mannose in a volume of 0.4 ml at 37° C. for 30 min with gently shaking. 1 mM AMP was also included as a precaution against degradation of the substrate nucleotide sugar by contaminating enzymes (Waechter et al., 1977). The product was then extracted into organic solvent as described earlier for assay of glucosamine phosphate transferase (Kaushal et al., 1985), and the content of tritium was determined by evaporation of the solvent in glass vials, the addition of 5 ml of Liquiscint (National Diagnostics), and counting in a liquid scintillation counter. The product was characterized as mannosylmonophosphoryldolichol as by Lehrman et al., 1988.

Glucosidase II and mannosidase II were assayed by the hydrolysis of paranitrophenyl α-glucoside (Tabas et al., 1982) and paranitrophenyl α-mannoside (Tulsiani et al., 1982), respectively. Assays included 20 μg of membrane protein, 2.5 mM α-glycoside or 5.0 mM α-mannoside, 0.1% Nonidet P-40, and 0.05 M PIPES, pH 7.0, in a volume of 0.2 ml and were incubated at 37° C. for 2 h. 3 ml of 0.2 M sodium phosphate buffer, pH 11, was then added, and the formation of paranitrophenol was detected by measuring the absorbance at 410 nm.

5. Concanavalin A Binding Assays

Approximately 1.5×10$^5$ cells were plated in wells of a 24-well plate (Costar) and allowed to grow for 2 days in the presence of varying concentrations of inhibitor such that the monolayers were nearly confluent. The cells were rinsed twice with TBS (20 mM Tris-Cl, pH 7.4, 150 mM CaCl, 1 mM CaCl$_2$ and 1 mM MnCl$_2$), fixed with PBS plus 1% glutaraldehyde, and rinsed twice with TBS-BSA (TBS plus 1 mg/ml BSA). The cells were next incubated with 10 μg/ml ConA-horseradish peroxidase (Sigma) in TBS-BSA plus 10 mM α-methylglucoside for 15 min, washed twice with TBS-BSA, and incubated with TBS-BSA plus 0.1 M α-methylgalactoside for 20 min at ambient temperature, which was subsequently discarded. Specifically bound ConA-horseradish peroxidase was eluted with 250 μl of TBS-BSA plus 0.1 M α-methylmannoside for 20 min at ambient temperature, the wells were rinsed with an additional 250 μl of the same solution, and the two eluates were combined. The solution containing the eluted complexes was mixed with 2.5 ml of 0.012% hydrogen peroxide plus 0.4 mg/ml o-phenylenediamine, and the absorbance at 440 nm was measured after incubation for 30 min at ambient temperature.

After elution of the ConA-horseradish peroxidase complexes, the cells monolayers were incubated with 0.1% crystal violent for 30 min, washed thoroughly with water, dried in air, and the bound dye was eluted with 0.2% Nonidet P-40 for 30 min with gentle shaking (Gillies et al., 1986). The quantity of eluted dye was estimated by the absorbance at 590 nm and used as a measure of cell mass (Gillies et al., 1986). The quantity of eluted ConA-horseradish peroxidase was then divided by the quantity of eluted crystal violet to generate a relative value for ConA binding to the cells.

6. Preparation of $^3$H-Labeled Oligosaccharides

Cells were labeled with [$^3$H]mannose in either PBS or low glucose medium exactly as described (Tabas et al., 1982). Low glucose-labeled cells were harvested from plastic dishes into PBS. PBS-labeled cells were harvested from glass dishes directly into chloroform:methanol (2:1) (Rosner et al., 1982). After performing several experiments, the latter method appeared to give more consistent results, possibly due to reduced metabolism of oligosaccharide intermediates during preparation (Rosner et al., 1982). Dolichol oligosaccharides were extracted and cleaved with weak acid as described (Tabas et al., 1982). Oligosaccharides were reduced with NaBH$_4$ and purified as described by Mellis et al., 1981, except that purification by paper chromatography was replaced by treatment with Amberlite MB-3 resin (Hirani et al., 1986). The oligosaccharides were mixed with 10-20 beads of this resin in 0.5 ml of water for 30 min. If the resin became saturated as judged by the appearance of yellow color, more resin was added as required. Oligosaccharides were then recovered by evaporation of the aqueous solvent. Addition of excessive amounts of resin resulted in large losses of oligosaccharide.

7. High Pressure Liquid Chromatography of Oligosaccharides

HPLC was performed with a 30-cm Micropak AX-5 anion exchange column and an acetonitrile:water gradient as described earlier with the following modifications (Mellis et al., 1981). All samples were reduced with NaBH$_4$ and purified with Amberlite as described above. Failure to reduce the oligosaccharides or purify them resulted in drastic losses of material and poor column resolution and reproducibility. In addition, the column was periodically cleansed with 0.1 M potassium phosphate, pH 3.0. Oligosaccharides were dissolved in 25% water, loaded onto the column, and the column was run with this mixture for 15 min. The solvent mixture was then changed to 35% water over 1 min, and then a gradient of 35-65% water was run for 60 min, during which fractions were collected. The column was purged with pure water for 15 min before returning to the starting condition. The flow rate was 1 ml/min.

8. Analysis of Glycopeptides

Glycopeptides were prepared from [$^3$H]mannose-labeled cells by pronase digestion of the proteinaceous residue that remained after extraction of the dolichol-oligosaccharides as described by Tabas et al., 1982. Endo H, endo F, and peptide:N-glycosidase F digestions were performed as recommended by the suppliers. Glycopeptides and oligosaccharides were resolved with a 1.0×47 cm column of Bio-Gel P-4 chromatographed with 0.1 M NH$_4$HCO$_3$, which could be evaporated to recover the fractionated material.

B. RESULTS

1. Conditions for the Selection of Cells Resistant to Glycoprotein Processing Inhibitors In order to obtain populations of CHO cells that were resistant to either deoxymannojirimycin, castanospermine, or swainsonine, it was necessary to develop conditions under which the growth of normal cells was inhibited by these compounds. It was found that cells grown in the presence of levels of the compounds which were capable of inhibiting glycosylation (Elbein, 1987) exhibited no inhibition of growth. This finding indicated that under the conditions used, CHO cells remained viable despite an inability to process asparagine-linked oligosaccharides. Thus, by themselves these compounds did not form the basis for selections which could be used to isolate resistant CHO cells. However, it was possible to design suitable selection conditions by adding low concentrations of ConA to the medium containing the inhibitors. ConA is known to be toxic to CHO cells with a LD$_{90}$ in the range of 10-20 μg/ml (Stanley, 1983). ConA binds most tightly to oligosaccharides of the high mannose and hybrid type (Kornfeld et al., 1985), which are generally found on the surfaces of normal CHO cells in low quantities and result from incomplete processing of the oligosaccharides to the complex type (Li et al., 1979).

Since incubation of CHO cells with deoxymannojirimycin or castanospermine blocks normal processing to generate structures of the high mannose type, and incubation with swainsonine generates structures of the hybrid type (Schwarz et al., 1985), it was reasoned that cells incubated with any of these compounds would express additional ConA binding sites on their surfaces and become more sensitive than untreated cells to the toxic effects of ConA. It was found that at a concentration of 7.5 μg/ml, ConA had no effect of the growth of CHO cells. However, in the presence of swainsonine, deoxymannojirimycin, or castanospermine, this concentration of ConA was toxic. The concentration of ConA required for this effect varied among experiments from 5 to 10 μg/ml, possibly due to variations among different batches of calf or fetal bovine serum which contained ConA-binding glycoproteins. In those situations where the level of ConA in the medium was either too high or too low, as judged by viewing the condition of the cells by phase-contrast microscopy after a few days of growth, it was possible to adjust the final concentration of ConA by adding medium without ConA or with 20 μg/ml ConA as required.

The dependence of the toxicity upon the concentration of inhibitor also tested. In this case, 5 μg/ml ConA was sufficient for inhibitor-dependent toxicity. Deoxymannojirimycin and castanospermine were toxic at 50 and 150 μg/ml, respectively. Swainsonine was toxic at all concentrations tested, although treatment with swainsonine did not always result in complete killing. This may have been related to somewhat weaker binding of ConA to the hybrid structures generated after swainsonine treatment as opposed to high mannose structures after deoxymannojirimycin or castanospermine treatment (Schwarz et al., 1985). Since deoxymannojirimycin, castanospermine, and swainsonine were toxic at concentrations known to inhibit glycoprotein processing (Elbein, 1987), the growth inhibition observed was likely to be directly related to the inhibition of the enzymes involved in glycoprotein processing. Furthermore, these results indicated that by combining ConA and glycoprotein processing inhibitors at concentrations that would inhibit growth, but not kill the cells, it would be possible to gradually select CHO cells in which the action of the processing enzymes had been altered.

2. Isolation of Castanospermine and Swainsonine-resistant Cell Populations

Selections were initiated by plating normal CHO cells in media containing 7 μg/ml ConA and 40 μg/ml castanospermine, 40 μg/ml deoxymannojirimycin, or 1 μg/ml swainsonine. Under these conditions, the colonies that grew were smaller than normal, and the cells were not as elongated as normal cells. Cells were grown under these conditions for ~4 weeks, until a large proportion of the cells regained a nearly normal morphology. Inhibitor concentrations were then raised 2-3 fold, and the cells were again allowed to recover.

This process was repeated a number of times over 5 months. In this way, cells that were resistant to high concentrations of each inhibitor could be obtained. The highest resistance to deoxymannojirimycin that could be achieved was at 500 μg/ml. Control experiments indicated that this amount of deoxymannojirimycin was toxic to control cells in the absence of ConA, suggesting that a nonspecific toxicity to high concentrations of deoxymannojirimycin was involved. Thus, the deoxymannojirimycin-resistant cell populations were not characterized further. However, resistance at much higher levels was achieved with castanospermine and swainsonine. Resistant cell populations were obtained at the highest concentrations used, 1000 μg/ml castanospermine and 100 μg/ml swainsonine. These cell populations were termed CsR-1000 and SwR-100, respectively.

Both the CsR-1000 and SwR-100 cell populations had morphologies that differed from the parental CHO cells. When viewed by phase-contrast microscopy the CsR-100- and SwR-100 cells were similar to each other, but were smaller in size than the CHO cells, especially at the centers of colonies, where the density of resistant cells was approximately twice that of normal cells. The CHO, CsR-1000, and SwR-100 cells grew equally well at 37° and 39° C., and slightly more slowly at 32° C., indicating the absence of a temperature-sensitive phenotype in these cell populations.

3. Pleiotropic Resistance to Glycoprotein Processing Inhibitors

Further analysis of the resistant cells revealed that the CsR-1000 cells and SwR-100 cells were each resistant to castanospermine and swainsonine. Furthermore, both cell types were also slightly resistant to deoxymannojirimycin. Thus, a pleiotropic form of processing inhibitor resistance appeared to be involved. This could not be attributed to any obvious changes in the assembly of the asparagine-linked oligosaccharides or to the involvement of multiple-drug resistance. Compared with the parental CHO cells, both resistant cell types were approximately 3-fold resistant to deoxymannojirimycin, 10-fold resistant to castanospermine, and 100-fold resistant to swainsonine. In this regard, the CsR-1000 and SwR-100 cells were essentially indistinguishable.

Figure 1A:
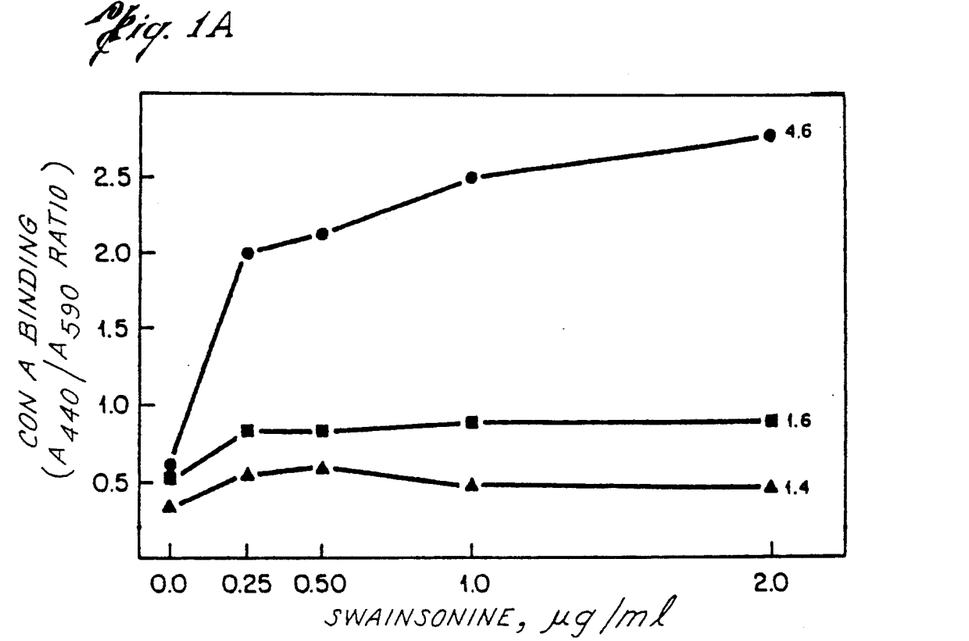
Figure 1B:
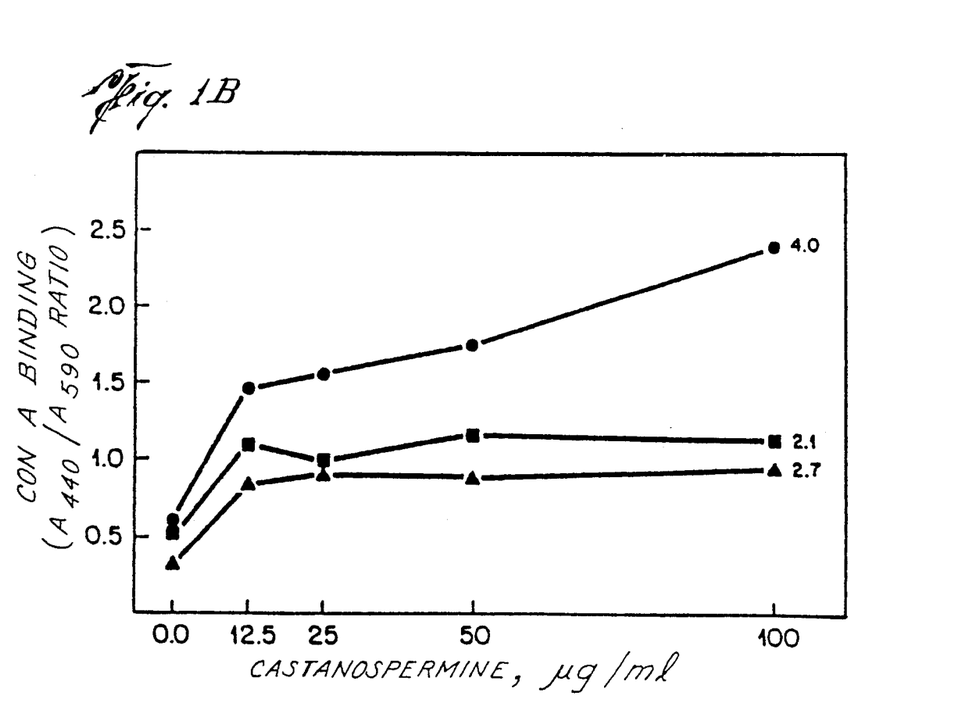

A more quantitative analysis of the inhibitor resistance is shown in FIG. 1. In this study, cells were grown to confluence in the presence or absence of swainsonine or castanospermine, fixed with glutaraldehyde, and incubated with a ConA-horseradish peroxidase conjugate in the presence of 10 mM α-methylglucoside to allow selective binding to high mannose and hybrid, but not complex oligosaccharides. After washing the monolayers to remove unbound conjugate, the specifically bound conjugate was eluted with α-methylmannoside and measured by a chromogenic reactions for horseradish peroxidase. The amount of conjugate recovered was normalized to the amount of cell mass as determined by the binding and subsequent elution of crystal violet (Gillies et al., 1986). As shown, the control cells bound 4.6-fold the amount of conjugate when grown in the presence of swainsonine as compared to growth in the absence of swainsonine. In contrast, the binding of conjugate to the CsR-1000 and SwR-100 cells increased only by one half when the cells were grown in the presence of swainsonine. As for swainsonine, control cells grown in the presence of castanospermine also showed a large increase in the amount of ConA-horseradish peroxidase bound. The CsR and SwR cells were resistant to castanospermine, although the degree of resistance was not high as for swainsonine. The effect of deoxymannojirimycin on ConA-horseradish peroxidase binding was not tested for since, for reasons which remain unclear, this conjugate failed to reproducibly show increased binding to control cells grown with deoxymannojirimycin.

4. Alterations in the Assembly of Dolichol Pyrophosphate-linked Oligosaccharides in Castanospermine and Swainsonine-resistant Cells Although studies had indicated that the cell surface oligosaccharides in the resistant cells were essentially normal, it remained possible that the dolichol-linked oligosaccharides were in some ways structurally altered. It has been shown previously that in cells containing certain mutations, altered dolichol-oligosaccharides could still give rise to normal protein-bound oligosaccharides by an alternate pathway (Kornfeld et al., 1979). In other cases, structurally abnormal dolichololigosaccharides also conferred resistance to N-methyl-1-deoxynojirimycin, an inhibitor related to castanospermine, by eliminating the requirement for glucosidase during the production of normal mature oligosaccharides (Romero et al., 1986).

In order to characterize the dolichol oligosaccharides in the resistant and parental CHO cells, cells were incubated for 30 min with [$^3$H]mannose, harvested, and differentially extracted to obtain two dolichol-oligosaccharide pools, one enriched for oligosaccharides of seven or more sugars (pool A), and the other enriched for oligosaccharides of less than seven sugars (pool B) (Tabas et al., 1982). The oligosaccharides were then cleaved from the lipid with weak acid (Tabas et al., 1982), reduced with sodium borohydride to yield the corresponding oligosaccharyl alcohols, and characterized by an HPLC system in which the largest oligosaccharides had the longest retention times and oligosaccharides differing by single monosaccharides were resolved into regularly space peaks (Mellis et al., 1981).

In the initial studies, cells were incubated in PBS during the 30-min labeling period. This procedure has been reported to give higher amounts of radiolabeled material than labeling in the presence of growth media (Tabas et al., 1982). Pool A from the parental CHO cells yielded one major peak (peak 1) which migrated slightly behind a $Glc_3Man_9GlcNAc$ standard partial digestion of this material with yeast α-glucosidase formed two additional peaks that migrated just ahead of peak 1. These results indicated that peak 1 most likely contained $Glc_3Man_9GlcNAc_2$, which is the major type of dolichol-linked oligosaccharide known to exist at steady state in CHO cells (Kornfeld, 1985). In contrast, very little material in pool A from CsR-1000 or SwR-100 cells was observed comigrating with peak 1.

In the pool A fractions from both CsR-1000 and SwR-100 cells a much more rapidly eluting oligosaccharide was observed (peak 2). This oligosaccharide was resistant to o-glucosidase digestion. A $Man_5GlcNAc_2$ standard migrated ahead of peak 2 by the equivalent of one monosaccharide, suggesting that peak 2 consisted of $Man_5GlcNAc_2$. In the CsR-1000 and SwR-100 samples, a number of other smaller peaks migrating ahead of and behind peak 2 was observed. Furthermore, in all samples a peak was observed eluting near the position of monosaccharide. These other species were not characterized further. It is possible that the monosaccharide-like material arose either from free mannose or Man-P-Dol that was not removed during extraction.

Taken together, the results obtained by the inventors indicated that the CsR-1000 and SwR-100 cells differed from the parental CHO cells by synthesizing primarily $Man_5GlcNAc_2$-pyrophosphoryl dolichol, which is normally an intermediate in the biosynthesis of $Glc_3Man_9GlcNAc_2$-pyrophosphoryl dolichol. It was also found that these oligosaccharides were transferred to protein. Thus, they were capable of being processed into normal mature cell surface oligosaccharides, but eliminated the requirements for glucosidase I and II (inhibited by castanospermine) and mannosidase II (inhibited by swainsonine), as well as reducing the requirement for mannosidase I (inhibited by deoxymannojirimycin), to confer upon the CsR-1000 and SwR-100 cells the observed pleiotropic resistance to glycoprotein processing inhibitors.

EXAMPLE II

Preparation of CHO Cell Lines Producing $Man_3GlcNAc_2$ Asparagine-Linked Glycans The preparation of CHO cell lines, termed PIR cells, having a defect which results in the accumulation of $Man_5GlcNAc_2$-P-P-dolichol was described in Example I. The present example describes CHO lines with both a PIR defect, as well as a second defect resulting in defective N-acetylglucosaminyltransferase I activity. Importantly, the resultant cells are found to synthesize asparagine-linked glycans with the structure $Man_3GlcNAc_2$. As a result, the asparagine-linked glycans produced by these lines are smaller and less heterogeneous than those produced by other currently available animal cell lines.

A. MATERIALS AND METHODS

1. Reagents

Ham's F-12 medium (powdered form), calf serum, fetal bovine serum, and G418 sulfate (Geneticin) were from Gibco. Hygromycin was from Calbiochem. Concanavalin A (Con A), *Phaseolus vulgaris* erythroagglutinin and leucoagglutinin (PHA-E and PHA-L), Lens culinaris agglutinin (LCA), polybrene, polyethylene glycol 1000, swainsonine, and pronase E were from Sigma. *Phaseolus vulgaris* leucoagglutinin (PHA-L)-agarose was from E-Y Laboratories. 1,4-diaminobutane (DAB) was from Aldrich. HPLC-grade isopropanol and Adsorbosphere HS Silica 3 micron columns were from Alltech. Acetonitrile (HPLC grade) was from Burdick and Jackson. Biogel P-4 resin was from Bio-Rad. Endoglycosidase D (Endo D) was from Boehringer Mannheim. Peptide-$N^4$-[N-acetyl-beta-glucosaminyl] asparagine amidase (N-glycanase) and deoxymannojirimycin (Dmn) was from Genzyme. [$2\text{-}^3$H]mannose (23.5 Ci/mmol) was from Dupont/New England Nuclear.

2. Cell Culture

CHO-K1 (control) cells and the PIR line SwR-100 are described in Example I (see also, Lehrman et al., 1989). The CHO mutant 15B (Gottlieb et al., 1975) was obtained from Dr. Stuart Kornfeld, Washington University, St. Louis, Mo. Cells were maintained in F-12 medium buffered to pH 7.2 with 15 mM sodium-HEPES and containing 2% fetal bovine serum, 8% calf serum, 100 units/ml penicillin, and 100 ug/ml streptomycin in a water-saturated 5% carbon-dioxide atmosphere at 37° C. In some studies requiring lectin selection the serum compositions were modified as described to reduce interference by serum glycoproteins.

3. Isolation of Mutant Lines

The mutants described in this example were all derived from PIR cells by selection for resistance to PHA-E, and individual PHA-E-resistant colonies were designated by the prefix PIR-P. PIR-P cells were found to have swainsonine-independent PHA-E resistance, and were obtained during attempts to screen for PIR cells that had acquired normal PIR gene activity after transfection with genomic DNA of CHO cells as judged by the aquisition of swainsonine-dependent resistance to PHA-E (Example I; Lehrman et al., 1989). After selecting approximately $2.7 \times 10^7$ cells at $2 \times 10^5$ cells per 10 cm dish in F-12 medium containing 3% calf serum, 20 ug/ml PHA-E and 1 ug/ml swainsonine for 8-10 days, 8 colonies designated PIR-P(1-8) were found to survive. Each of these was reselected under these conditions for several passages. In all cases, resistance to PHA-E was found to be independent of the presence of swainsonine. The PIR-P3 and PIR-P8 lines characterized in this study were shown to be free of mycoplasma contamination as judged by the MycoTect test (Gibco).

4. PHA-L-Agarose Chromatography of Glycopeptides

Glycopeptides were prepared by labeling 10 cm dishes of cells at 60-80% confluence with 0.2 mCi [$^3$H]mannose in 5 ml normal medium for 24 hours, extracting with organic solvents, and incubating with pronase as described by Tabas et al., 1982. The glycopeptides were purified on a Sephadex G-25 column (0.7×30 cm) equilibrated in water, dried under nitrogen, and dissolved in 6.7 mM sodium phosphate, pH 7.4, containing 0.15 M sodium chloride and 0.02% sodium azide. 100 ul of glycopeptide solution was loaded onto a PHA-L agarose column (0.3×35 cm) equilibrated in phosphate buffer and eluted at a flow rate of 2 ml/hr. Fractions of 0.5 ml were collected and counted. The recovery of [$^3$H]-oligosaccharides was at least 80%.

5. N-Glycanase Digestion and Biogel P-4 Chromatography

Cells were labeled as described for glycopeptide preparation, and membranes were prepared exactly as described by Lehrman et al., 1988. After washing the membranes several times with water they were dissolved in 250 ul 0.2% NP-40 and sonicated until the solution was clear. For N-glycanase digestion, 15 ul of membrane extract was mixed with 12.5 ul 0.5% SDS, 13 ul 0.55 M sodium phosphate, pH 8.6, 4 ul 100 mM 1,10-phenanthroline, 1 ul 35% NP-40, and 1.5 ul (0.38 units) N-glycanase. After incubation at 37° C. for 24 hours, the sample was mixed with 200 ul water, clarified in a microfuge, and loaded onto a 1×47 cm Biogel P-4 column equilibrated in 0.1 M ammonium bicarbonate. Fractions of 1 ml were collected and 25 ul portions were counted. Fractions containing oligosaccharides were combined and dried under nitrogen.

6. Endoglycosidase D Digestion

Glycopeptides were digested with pronase as described above for PHA-L chromatography, adsorbed onto a 19.3 mg/ml Concanavalin A-agarose column, eluted with 0.4 M alpha-methylmannoside, concentrated to a volume of 0.5 ml, and purified on a Biogel P-4 column as described above. For endo D digests, about 50,000 c.p.m. of glycopeptide was evaporated to dryness under nitrogen, redissolved in 10 ul water, mixed with 10 ul 0.15 M sodium citrate-phosphate, pH 6.5, 10 ul 0.1 M NaCl containing 0.1% BSA, and 1.5 ul (1 mU/ul) endo D, and incubated at 37° C. for 24 hours. After addition of 100 ul water, the digest was fractionated on a Biogel P-4 column as described above and fractions containing oligosaccharides were collected.

7. High Pressure Liquid Chromatography (HPLC) of Oligosaccharide

P-4 column chromatography were repeatedly dissolved in a small volume of water and evaporated to dryness under nitrogen for 3 to 4 cycles, and then reduced and purified as described for dolichol-linked oligosaccharides (see Example I and Lehrman et al., 1989). Oligosaccharides obtained after N-glycanase digestion were treated similarly, except that residual NP-40 was removed prior to the first cycle of drying by partitioning with 1 ml each of water and chloroform.

HPLC was performed with a 15 cm. Alltech Adsorbosphere 3 micron silica column eluted with a water-/acetonitrile gradient containing diaminobutane (preconditioned with a silica saturation column) essentially as described by Turco et al., 1981, with modifications as described by Plantner et al, 1988. Solvent A was water plus 0.2 % diaminobutane and solvent B was 90% acetonitrile, 10% water, and 0.2% diaminobutane. Oligosaccharides were dissolved in 25% water/75% acetonitrile and loaded onto the column equilibrated with 20% A / 80% B. At a flow rate of 1 ml/min, the column was then eluted with 20% A for 9 min., a linear gradient of 20%–30% A for 1 min., and then a linear gradient of 30%–55% A for 75 min at which point fractions of 1 ml were collected and counted. The column was cleansed periodically with isopropanol.

8. Transfection and Cell Fusion

Cells were transfected to G418 resistance or to hygromycin resistance by the polybrene procedure (Chaney et al., 1986) as described in Zeng et al., 1990. Positive colonies were isolated and reselected for drug resistance. Cell hybrids were formed with polyethylene glycol 1000 and selected exactly as described by Zeng et al., 1990. Con A resistance was tested at 0, 5, 7.5, and 10 ug/ml with 10% fetal bovine serum, and PHA-E resistance was tested at 0, 10, 20, and 40 ug/ml with 1% calf serum. Unhybridized parental cells were tested similarly, but with only the drug to which they were resistant. After incubation at 37° C. for 8 days cells were stained with crystal violet.

B. RESULTS

In contrast to normal CHO cells, which synthesize Glc$_3$Man$_9$GlcNAc$_2$-P-P-dolichol, CHO mutants of the PIR complementation group synthesize primarily Man$_5$GlcNAc$_2$-P-P-dolichol (FIG. 2) (see Example I). The abnormal oligosaccharides in PIR cells are efficiently transferred to asparagine residues of proteins and are then substrates for processing glycosidases and glycosyltransferases. As judged by lectin sensitivity, cell surface oligosaccharides that are expressed by PIR cells are similar to those found on normal CHO cells.

1. Isolation of Double-Mutants by PHA-E Resistance

As described in the above methodology section, eight colonies of PIR cells that had acquired resistance to 20 ug/ml PHA-E, which binds complex type structures (Cummings et al., 1982; Green et al., 1987), were isolated and designated PIR-P(1–8 ). The resistance to PHA-E was not dependent upon the presence of swainsonine, which blocks synthesis of complex oligosaccharides in normal cells (Lehrman et al., 1989; Elbein, 1987), indicating that these were not PIR cells that had reverted to normal phenotype. Analysis of dolichol-linked oligosaccharides in the PIR-P mutants indicated that they accumulated Man$_5$GlcNAc$_2$-P-P-dolichol to the same extent as the parental PIR cells. Each isolate was then screened for sensitivity to the lectins Con A, LCA, PHA-E, and PHA-L. Three mutants, designated PIR-P3, PIR-P6, and PIR-P8 had 5-fold sensitivity to Con A with respect to normal CHO cells and resistance to at least 200 ug/ml of LCA, PHA-E, and PHA-L, suggestive of an absence of complex type glycans. PIR-P3 and PIR-P8 were selected for further analysis (see below). Their growth rates did not appear to differ significantly from those of PIR cells. The remaining mutants had lectin sensitivities that differed from PIR-P(3,6,8) and were not characterized further.

2. Genotypic analysis of N-acetylglucosaminyltransferase I deficiency

Figure 2:
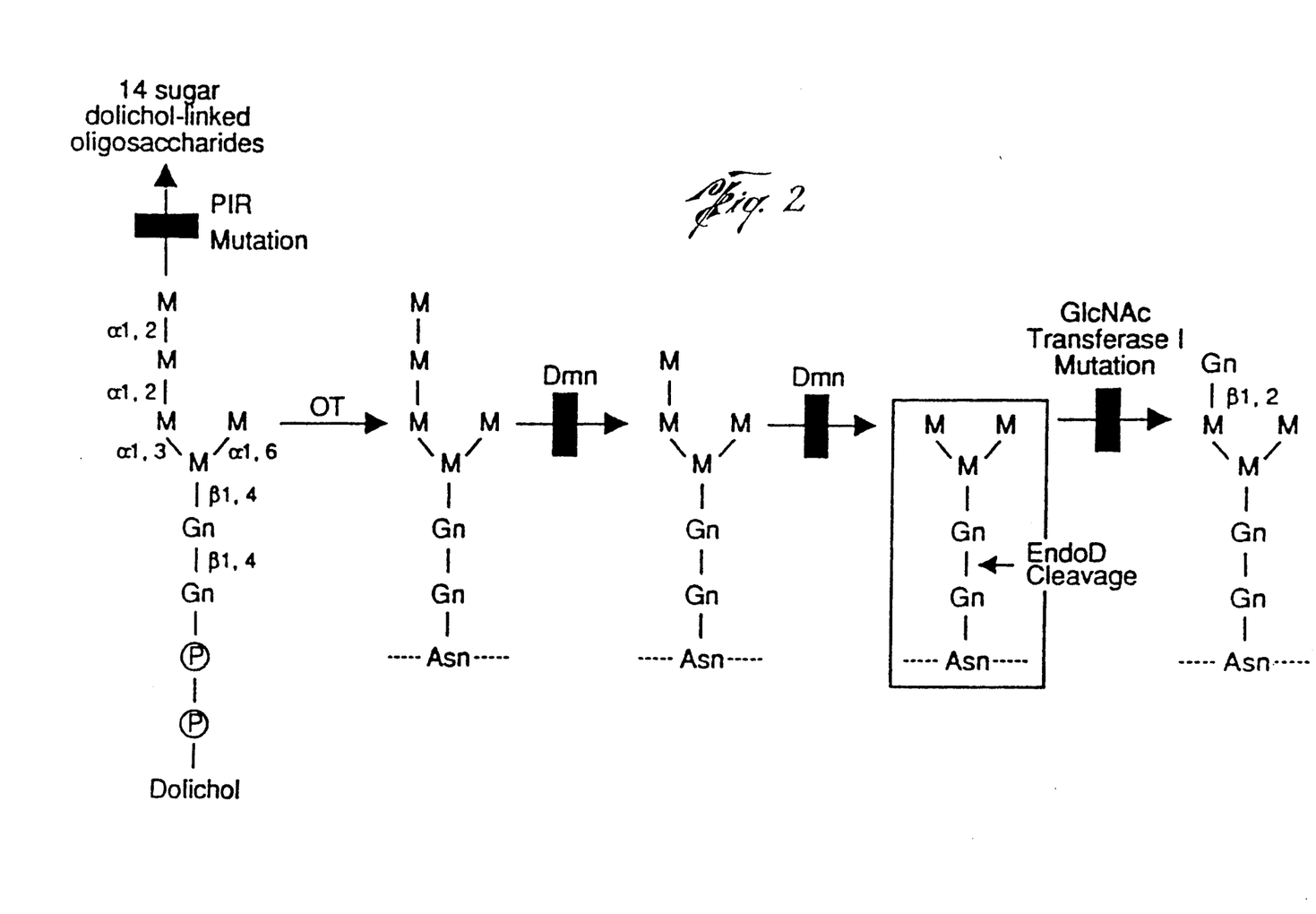

The results described above suggested that PIR-P3 and PIR-P8 had a defect in one of the glycosyltransferases of the Golgi complex. A defect in N-acetylglucosaminyltransferase I was suspected since a loss of this enzyme in a PIR background would be expected to give the lectin sensitivities observed for PIR-P(3,6,8) due to trimming of the Man$_5$GlcNAc$_2$ glycan to Man$_3$GlcNAc$_2$ without subsequent extension by glycosyltransferases (FIG. 2).

To determine whether a N-acetylglucosaminyltransferase I defect was responsible for the observed phenotype in PIR-P3 cells, they were hybridized with 15B cells, a line of CHO cells known to have defective N-acetylglucosaminyltransferase I activity (Gottlieb et al., 1975). Since the PIR mutation in the PIR-P3 cells is recessive (Zeng et al., 1990), it would be corrected upon fusion with 15B cells. Thus, it was only necessary to test hybrids for 15B/PIR-P3 phenotypes such as growth sensitivity to Con A and resistance to PHA-E. As shown in Table I, the phenotypic properties of homologously fused hybrids of PIR, PIR-P3, and 15B cells were identical to those of the unfused parental cells, indicating that sensitivity or resistance of these cells to lectins was not altered by hybridization. The PIR-P3 defect was recessive because fusion with parental PIR cells gave hybrids lacking the 15B/PIR-P3 phenotype. In contrast, hybrids formed between 15B and PIR-P3 retained a 15B/PIR-P3 phenotype. This demonstrated that PIR-P3 lacked N-acetylglucosaminyltransferase I activity and that the same gene was defective in 15B cells.

TABLE I
Complementation Analysis of PIR-P3 Cells

| Cells Tested | Cell Viability | | PIR-P3 Phenotype |
|---|---|---|---|
| | 40 ug/ml PHA-E | 10 ug/ml Con A | |
| Parental: | | | |
| PIR | − | + | No |
| 15B | + | − | Yes |
| PIR-P3 | + | − | Yes |
| Hybrid: | | | |
| PIR × PIR-P3 | − | + | No |
| 15B × PIR-P3 | + | − | Yes |
| PIR × PIR | − | + | No |
| 15B × 15B | + | − | Yes |
| PIR-P3 × PIR-P3 | + | − | Yes |

Parental and hybrid cells were tested for lectin sensitivity as described in the methodology section. The results shown here summarize a collection of experiments, and in each case approximately 50-100 colonies were screened in wells of a 24-well plate. A (+) indicates that colony growth in the presence of lectin was equivalent to that in the absence of lectin; a (−) indicates that no colonies grew in the presence of lectin.
Hybrids were tested for lectin resistance immediately after fusion, and no hybrids were found if polyethylene glycol 1000 was omitted. Fusions involving two different cell types were performed with both possible combinations of G418 and hygromycin resistance.

3. Analysis of PIR-P3 and PIR-P8 Oligosaccharides by HPLC

To determine the extent to which Man$_3$GlcNAc$_2$ glycans were accumulating in PIR-P3 and PIR-P8, cells were labeled for 24 hours with [$^3$H]mannose and total cellular glycoproteins were digested with N-glycanase. After recovery from Biogel P-4 columns, the released [$^3$H]-oligosaccharides were reduced with sodium borohydride and fractionated by HPLC.

Figure 3A:
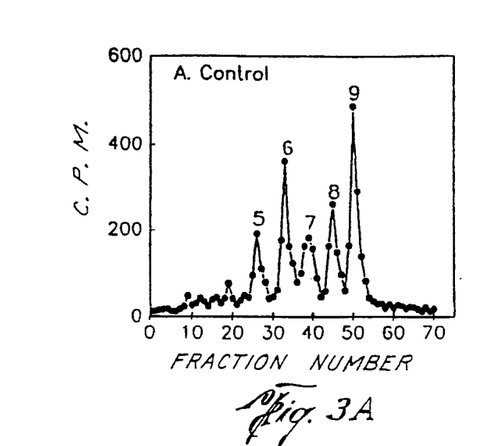
Figure 3B:
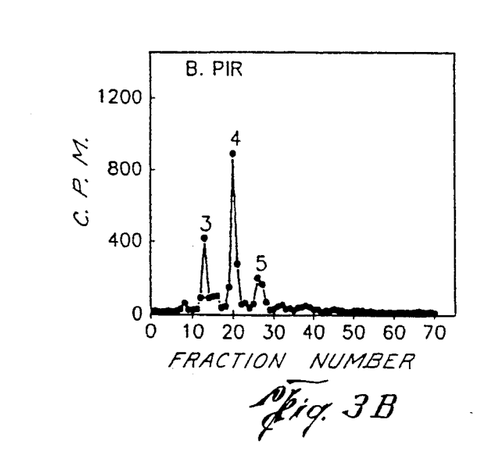
Figure 3C:
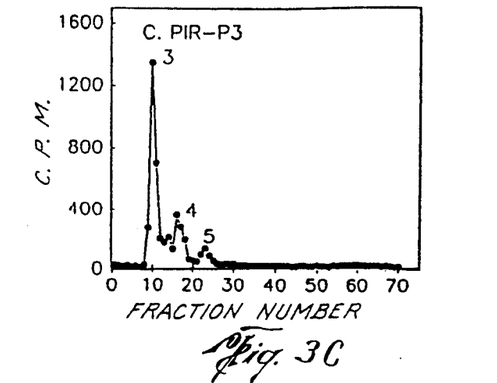
Figure 3D:
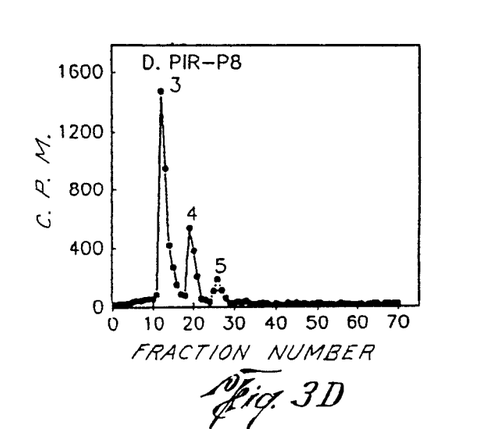

N-glycanase was able to release 35%, 35%, 71%, and 82% of the [$^3$H]label from the CHO, PIR, PIR-P3 and PIR-P8 glycoproteins, respectively, and repeat digestion released no additional material. The enhanced release from PIR-P3 and PIR-P8 may reflect a preference for smaller glycans such as Man$_3$GlcNAc$_2$ by N-glycanase. HPLC analysis of the released glycans is shown in FIG. 3. This HPLC system resolves neutral oligosaccharides on the basis of size (Turco et al., 1981; Plantner et al., 1988). Apparently, negatively charged complex oligosaccharides are not recovered from the column since only high-mannose oligosaccharides were observed in N-glycanase digests from CHO and PIR cells (FIG. 3, panels A and B).

CHO cells displayed the expected high-mannose type glycans containing 5-9 mannose residues (FIG. 3, panel A). On the other hand, PIR cells displayed species with 3, 4, or 5 mannose residues (FIG. 3, Panel B). In both cases, the results were indicative of N-linked glycans which were either inefficiently trimmed by ER and Golgi mannosidases or were not yet modified by N-acetylglucosaminyltransferase I. Both PIR-P3 and PIR-P8, however, gave mostly Man$_3$GlcNAc$_2$ (FIG. 3, Panels C and D). The two remaining peaks corresponding to 4 and 5 mannose residues appear to result from incomplete mannosidase digestion (see below). By normalizing the peak areas to the number of mannose residues per chain, we estimate that 70-75% of the glycans contain 3 mannose residues.

Since the HPLC analysis could not determine the extent to which production of complex oligosaccharides was blocked in PIR-P3 and PIR-P8, [$^3$H]mannose-labeled glycopeptides were subjected to chromatography on a column of PHA-L lectin, which specifically binds to complex structures (Cummings et al., 1982; Green et al., 1987). As expected (FIG. 4), CHO (Panel A) and PIR (Panel B) cells gave peaks corresponding to both high-mannose (fractions 5-7) and complex (fractions 9-20) structures. 15B cells, which lack N-acetylglucosaminyltransferase I, do not synthesize complex structures (Panel C). The profiles obtained with both PIR-P3 (Panel D) and PIR-P8 (Panel E) glycopeptides were indistinguishable from that of 15B cells, demonstrating that little or no complex oligosaccharides were made in these cells.

4. Effect of deoxymannojirimycin on PIR-P8 cells

Figure 3E:
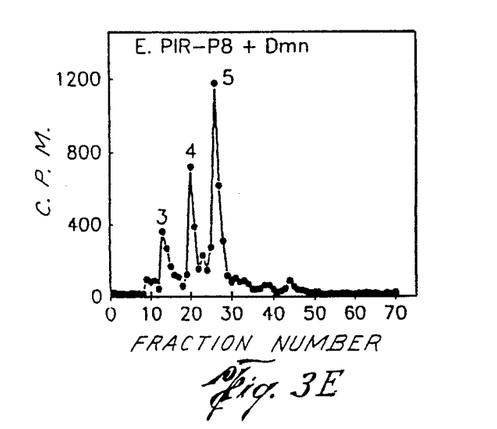
Figure 4A:
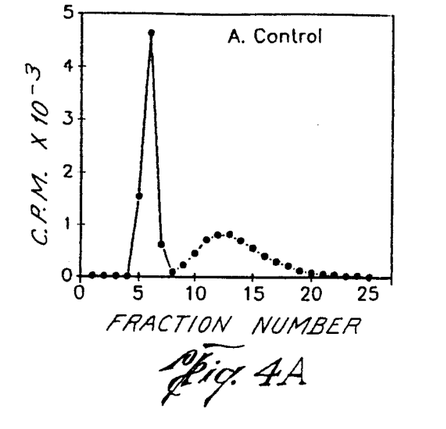
Figure 4B:
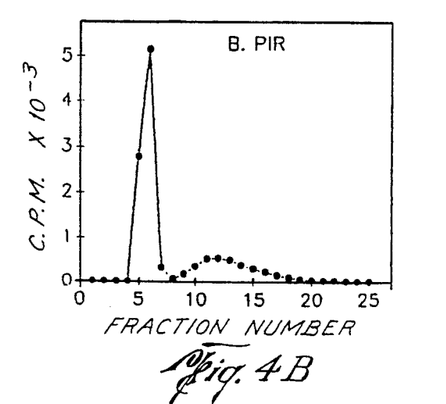
Figure 4C:
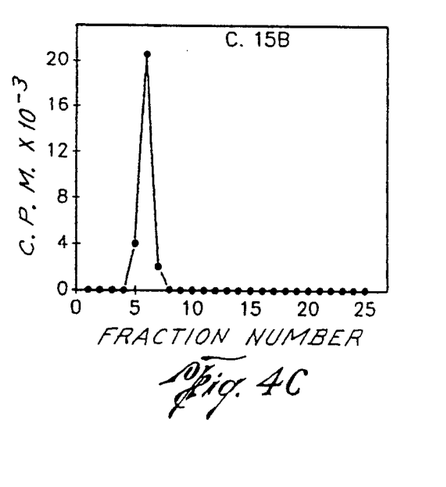
Figure 4D:
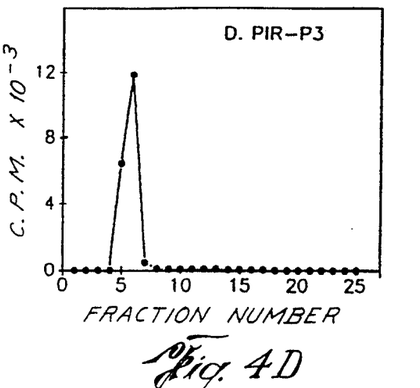
Figure 4E:
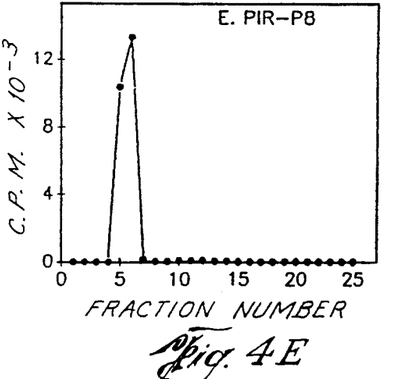
Figure 5A:
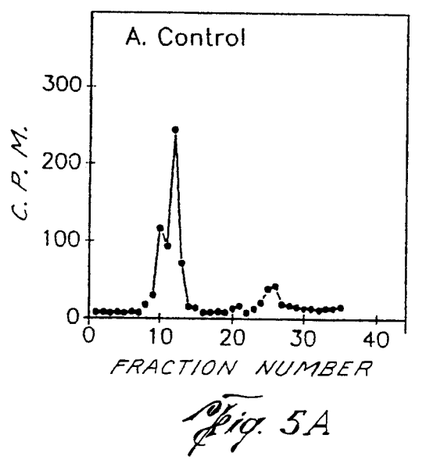
Figure 5B:
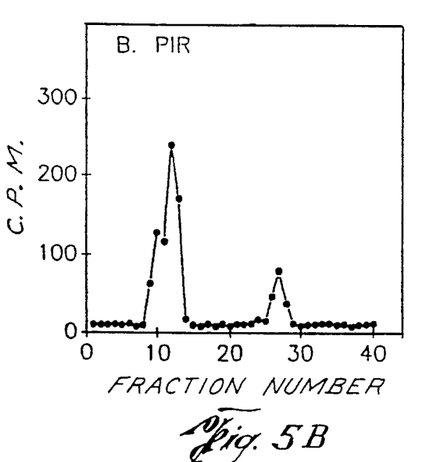
Figure 5C:
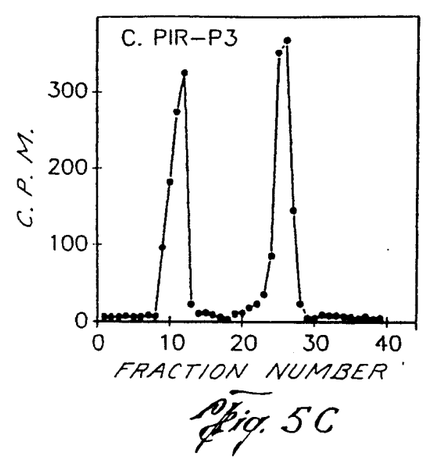
Figure 5D:
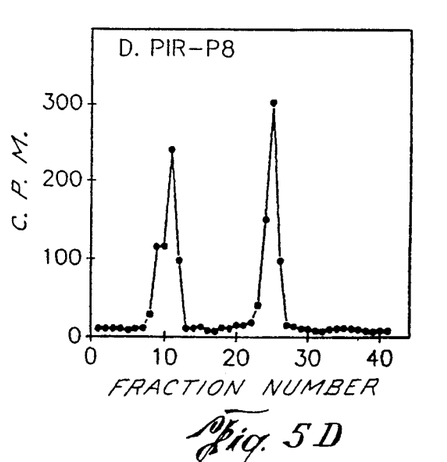

Deoxymannojirimycin (Dmn) is a specific inhibitor of Golgi mannosidase I (Elbein et al., 1987; Bischoff et al., 1984) which is required for efficient trimming of mannose residues in CHO cells. To demonstrate that the Man$_3$GlcNAc$_2$ glycan was derived from Man$_5$GlcNAc$_2$ by the normal processing pathway, PIR-P8 cells were incubated with Dmn prior to labeling and analysis of the oligosaccharides. As shown in FIG. 3 (Panel E), incubation of PIR-P8 cells with 100 ug/ml Dmn decreased the amount of the trimannosyl form and gave a corresponding increase in the pentamannosyl form. Thus, the normal processing pathway appeared to be involved, although the inability of Dmn to give complete inhibition could indicate minor contributions by other mannosidases.

5. Digestion of glycopeptides with endoglycosidase D

From the known oligosaccharide processing pathways in CHO and PIR cells and results of HPLC analysis (FIG. 3), the structure of the major oligosaccharide in PIR-P3 and PIR-P8 cells could be deduced (FIG. 2). This trimannosyl structure, Man$\alpha$1,3(Man$\alpha$1,6)Man$\beta$1,4GlcNAc$\beta$1,4GlcNAc, should be susceptible to endoglycosidase D digestion, which requires that the alpha 1,3-linked mannose be unsubstituted (Maley et al., 1989). As shown in FIG. 5, glycopeptides from CHO and PIR cells were mostly resistant to endo D. The small fraction that was susceptable was probably due to structures that were trimmed to expose the alpha 1,3-linked mannose but not modified further by N-acetylglucosaminyltransferase I. In contrast, about half of the label in glycopeptides from PIR-P3 and PIR-P8 cells was susceptable to endo D cleavage. The increased quantity of endo D-sensitive glycopeptides is the expected consequence of a N-acetylglucosaminyltransferase I defect.

The endo D-susceptable glycans from each cell were then characterized by HPLC. In accord with the known processing pathways, CHO cells produced a single peak corresponding to $Man_5GlcNAc$ and PIR cells produced a single peak corresponding to $Man_3GlcNAc$, the only endo D-susceptable products expected from these cells. PIR-P3 and PIR-P8 produced only the trimannosyl species, like PIR cells, but in much larger quantities as shown in FIG. 5. The $Man_3GlcNAc_2$ oligosaccharide is therefore the major N-linked glycan produced by PIR-P3 and PIR-P8.

C. DISCUSSION

This example demonstrates the isolation and characterization of cell lines capable of producing a small and relatively homogeneous population of N-linked glycans. The two lines characterized here, PIR-P3 and PIR-P8, appear to have similar or identical genotypes affecting both the PIR and N-acetylglucosaminyltransferase I genes. As a result, 70-75% of their N-linked glycans have the structure $Man_3GlcNAc_2$. The remaining glycans have either 1 or 2 additional mannose residues.

The PIR-P3 and PIR-P8 lines produce N-linked glycans that are smaller and/or less heterogeneous than other animal cell lines. In the $C_6/36$ mosquito cell line, which does not synthesize complex-type oligosaccharides, approximately half of the N-linked glycans had the structure $Man_3GlcNAc_2$, with the remainder consisting of 5-9 mannose residues (Hsieh et al., 1984). Presumably, the latter fraction resulted from incomplete trimming of precursors containing 9 mannose residues. A CHO line carrying the Lec1 and Lec6 mutations (Stanley, 1984; Hunt, 1980) was shown to produce glucosylated $Man_7GlcNAc_2$-P-P-dolichol which eventually gave rise to N-linked glycans with 4 mannose residues due to defective N-acetylglucosaminyltransferase I. However, there was also significant accumulation of oligosaccharides with 5-7 mannose residues, presumably due to incomplete trimming. Several other CHO lines have also been described carrying the Lec1 mutation in combination with others mutations (Stanley, 1989), but the smallest N-linked glycan produced by these cells has 5 mannose residues. It should be noted, however, that while these lines reduce or eliminate the heterogeneity of O-linked glycans, no such advantage is expected in PIR-P3 or PIR-PB cells.

The PIR-P3 and PIR-P8 cells should prove useful in cases where the size and heterogeneity of N-linked glycans is undesirable, such as during production and purification of useful glycoproteins (discussed in Stanley, 1989), in biophysical studies of glycoproteins, or when the biological activity of a glycoprotein can be improved by modification with smaller glycans (for example, see Takeuchi et al., 1990). These cells are readily transfected with plasmids, making heterologous expression of glycoproteins possible. The causes of incomplete trimming of mannose residues in normal CHO cells, such as steric hindrance (Hubbard, 1988), will probably hold true in PIR-P3 and PIR-P8 cells. Thus, it is expected that glycoproteins that normally retain high-mannose oligosaccharides will have oligosaccharides with 4 or 5 mannose residues in PIR-P3 and PIR-P8, and glycoproteins that normally have hybrid or complex oligosaccharides will have $Man_3GlcNAc_2$.

D. ATCC DEPOSIT OF REPRESENTATIVE CELL LINE

Cell line PIR-P3 that is representative of cell lines in accordance with the present invention has been deposited with the American type culture collection, 12301 Parklawn Drive, Rockville, Md. 20852, USA, on Jun. 9, 1993, as ATCC accession number CRL 11378.

EXAMPLE III

Preparation of Recombinant CHO Lines Expressing EPO

PIR-P CHO lines expressing recombinant erythropoietin (EPO) are prepared as described in U.S. Pat. No. 4,703,008 (incorporated herein by reference), except employing a PIR-P CHO line prepared as described in Example II above. Briefly, an expression plasmid carrying the EPO coding sequence, such as plasmid pSVgHuEPO, is constructed as described in example 7 of U.S. Pat. No. 4,703,008. Then, plasmid pSVgHuEPO DNA is used to express human EPO material in PIR-P CHO cells by combining pSVgHuEPO DNA with carrier DNA and transfecting into triplicate plates of the CHO cells. As a control, carrier DNA alone is also transfected into CHO cells. Cell culture fluid is then sampled five and seven days later and tested for the presence of polypeptides possessing the immunological or biological properties of human EPO, such as according to the procedures described in example 2 of U.S. Pat. No. 4,703,008.

EXAMPLE IV

Preparation of Recombinant CHO Lines Expressing t-PA

PIR-P CHO lines expressing recombinant tPA can be prepared as described in U.S. Pat. No. 4,766,075. A plasmid comprising both the human t-PA coding sequence and a dihydrofolate reductase (DHFR) coding sequence, corresponding to plasmid pETPER disclosed in examples E.2.A and E.2.B of U.S. Pat. No. 4,766,075, is transfected into DHFR+PIR-P CHO cells by the method of Graham and Van der Eb (Virology, 52:456 (1973)). Transformed DHFR+ PIR-P cells are selected by growth in $\geq 100$ nM methotrexate (MTX). Colonies which arise are isolated using cloning rings and propagated in the same medium for several generations.

For amplification, cells from the colonies are split into media containing increasing amounts of MTX (e.g., ranging from about $5 \times 10^4$ nM to about $10^6$ nM) and passaged several times. Cells are plated at very low cell densities (e.g., on the order of $10^2$–$10^3$ cells/plate) in 10 cm dishes and the resulting colonies are isolated. Expression of t-PA in the transfected amplified colonies may conveniently be assayed by the methods set forth in example E.1.K.1.b of U.S. Pat. No. 4,766,075.

The present invention has been disclosed in terms of preferred modes found to work well in the practice of the invention. However, numerous modifications and changes in the steps, procedures used and material will become apparent to those of skill in the art in light of the disclosure. All such modifications are intended to be within the spirit of the present invention and scope of the appended claims.

REFERENCES

The following references are hereby incorporated by reference to the extent that they describe, explain, teach methodology for or provide useful materials or compositions for use in connection with the practice of the present invention, for the reasons specified in the foregoing text.

Bischoff, J., and Kornfeld, R. (1984), Biochem. and Biophys. Res. Com., 125:324–331.

Chaney, W. G., Howard, D. R., Pollard, J. W., Sallustio, S., and Stanley, P. (1986), Somatic Cell and Molecular Genetics, 12: 237–244.

Cummings, R., and Kornfeld, S. (1982), J. Biol. Chem., 257:11230–11234.

Darnell, J. E., Lodish, H., and Baltimore, D. (1986), Molecular Cell Biology, Scientific American Books, Inc., New York, pp. 957–964.

Elbein, A. (1987), Ann. Rev. Biochem., 56:497–534.

Gillies, R., Didier, N., and Denton, M. (1986), Anal. Biochem., 159:109–113.

Gottlieb, C., Baenziger, J., and Kornfeld, S. (1975), J. Biol. Chem., 250:3303–3309.

Green, E., and Baenziger, J. (1987), J. Biol. Chem., 262:12018–12029.

Hirani, S., and Rasmussen, J. (1986), Biol. Chem. HoppeSeyler, 367:191–194.

Hsieh, P., and Robbins, P. (1984), J. Biol. Chem., 259:2375–2382.

Hubbard, S. (198B), J. Biol. Chem., 263:19303–19317.

Hunt, L. (1980), ell, 21:407–415.

Kaushal, G. P., and Elbein, A. D. (1985), J. Biol. Chem., 260:16303–16309.

Kornfeld, S., Gregory, W., and Chapman, A. (1979), J. Biol. Chem., 254:11649–11654.

Kornfeld, R., and Kornfeld, S. (1985), Ann. Rev. Biochem., 54:631–664.

Lehrman, M. A., and Zeng, Y. (1989), J. Biol. Chem., 264:1584–1593.

Lehrman, M. A., Zhu, X., and Khounlo, S. (1988), J. Biol. Chem., 263:19796–19803.

Li, E., and Kornfeld, S. (1979), J. Biol. Chem., 254:1600–1605.

Maley, F., Trimble, R., Tarentino, A., and Plummer, J., T.H. (1989), Anal. Biochem., 180:195–204.

Mellis, S., and Baenziger, J. (1981), Anal. Biochem., 114:276–280.

Plantner, J., and Kean, E. (1988), Exp. Eye Res., 46:785–800.

Romero, P.A., and Herscovics, A. (1986), J. Biol. Chem., 261:15936–15940.

Rosner, M., Hubbard, S., Ivatt, R., and Robbins, P. (1982), Methods Enzymol., 83:399–409.

Schwarz, P.M., and Elbein, A.D. (1985), J. Biol. Chem., 260:14452–14458.

Spellman et al. (1989), Jrnl. Biol. Chem., 264:14100–14111.

Stanley P. (1983), Somatic Cell Genet., 9:593–608.

Stanley, P. (1984), Ann. Rev. Genet., 18:525–552.

Stanley, P. (1989), Molec. and Cell. Bio., 9:377–383.

Tabas, I., and Kornfeld, S. (1982), Methods in Enzymology., 83:416–429.

Takeuchi, M., Takasaki, S., Shimada, M., and Kobata, A. (1990), J. Biol. Chem., 265:12127–12130.

Tulsiani, D.R.P., Harris, T. M., and Touster, O. (1982), J. Biol. Chem., 257:7936–7939.

Turco, S. (198i), Anal. Biochem., 118:278–283.

Waechter, C., and Harford, J. (1977), Arch. Biochem. Biophys., 181:185–198.

Zeng, Y., and Lehrman, M. (1990), J. Biol. Chem., 265:2296–2305.

What is claimed is:

1. A method for preparing a CHO cell line producing $Man_3GlcNAc_2$ asparagine-linked glycans, comprising the steps of:
   (a) culturing a population of CHO cells which produce N-linked glycans, to provide a cell culture;
   (b) selecting cells from the cell culture that are resistant to one or more glycoprotein processing inhibitors, to provide a cell culture of PIR cells;
   (c) selecting from the culture of PIR cells, cells that are resistant to PHA-E, independent of the presence of swainsonine; and
   (d) culturing the swainsonine-independent PHA-E resistant PIR cells, to provide a cell line producing $Man_3GlcNAc_2$ asparagine-linked glycans.

2. The method of claim 1, wherein the cell line is further defined as a cell line which produces dolichol-linked oligosaccharides having 14 sugars.

3. The method of claim 1, wherein the PIR cells are selected using castanospermine or swainsonine.

4. The method of claim 1, wherein the PHA-E resistant cells are selected using PHA-E.

5. The method of claim 4, wherein the PHA-E resistant cells are selected using PHA-E and swainsonine.

6. The method of claim 1, wherein at least 60% of the glycosylated asparagine residues are $Man_3GlcNAc_2$-linked.

7. The method of claim 6, wherein at least 70% of the glycosylated asparagine residues are $Man_3GlcNAc_2$-linked.

8. A CHO cell line producing $Man_3GlcNAc_2$ asparagine-linked glycans, wherein at least 60% of the glycosylated asparagine residues are $Man_3GlcNAc_2$-linked.

9. A CHO cell line having a first and second defect in N-linked glycosylation, wherein the first defect results in an accumulation of $Man_5GlcNAc_2$-P-P-dolichol, and the second defect results in defective N-acetylglucosaminyltransferase I activity, the cell line producing $Man_3GlcNAc_2$ asparagine-linked glycans.

10. The cell line of claim 9, wherein the first defect comprises a PIR mutation.

11. The cell line of claim 9, further defined as a cell line which produces dolichol-linked oligosaccharides having 14 sugars.

12. The cell line of claim 9, wherein at least 60% of the glycosylated asparagine residues are $Man_3GlcNAc_2$-linked.

13. The cell line of claim 12, wherein at least 70% of the glycosylated asparagine residues are $Man_3GlcNAc_2$-linked.

14. The cell line of claim 9, further defined as a host cell.

15. The cell line of claim 14, wherein the host produces a glycosylated recombinant protein having $Man_3GlcNAc_2$-linked asparagine residues.

16. The cell line of claim 15, wherein the recombinant protein comprises tissue plasminogen activator or erythropoietin.

17. A CHO cell line having the following properties:
   (a) relative resistance to the action of glycoprotein processing inhibitors;
   (b) relative resistance to the action of PHA-E, independent of the presence of swainsonine; and
   (c) producing $Man_3GlcNAc_2$ asparagine-linked glycans.

18. The cell line of claim 17, wherein the cell line is resistant to 200 µg/ml of LCA, PHA-E or PHA-L.

* * * * *